(12) United States Patent
Red'kina

(10) Patent No.: US 6,468,779 B1
(45) Date of Patent: *Oct. 22, 2002

(54) AQUEOUS EXTRACT OF LEGUMES FOR GROWING AGRONOMICALLY BENEFICIAL MICROBES

(75) Inventor: Tatiana Vasilienva Red'kina, Moscow (RU)

(73) Assignee: Tatko Biotech, Inc., Peoria, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/370,436

(22) Filed: Aug. 9, 1999

Related U.S. Application Data

(63) Continuation-in-part of application No. 09/210,403, filed on Dec. 11, 1998, now Pat. No. 5,951,978.
(60) Provisional application No. 60/111,776, filed on Dec. 10, 1998.

(51) Int. Cl.⁷ .................. A01N 63/00; A01N 63/04; C12N 1/00; C12N 1/16; C12N 1/20
(52) U.S. Cl. ............... 435/243; 435/253.6; 435/255.7; 424/93.4; 424/93.5; 424/757
(58) Field of Search ............................. 435/252.1, 243, 435/415, 426, 252.2, 244, 878, 253.6, 255.7; 424/93.1, 757, 93.4, 93.5

(56) References Cited

U.S. PATENT DOCUMENTS

| | | | | | |
|---|---|---|---|---|---|
| 2,670,291 A | * | 2/1954 | Melnick | ......... | 99/91 |
| 4,486,459 A | * | 12/1984 | Thompson | ......... | 426/634 |
| 5,229,291 A | * | 7/1993 | Nielsen et al. | ......... | 435/252.2 |
| 5,955,082 A | * | 9/1999 | Bodnaryk et al. | ......... | 424/195.1 |

\* cited by examiner

*Primary Examiner*—David M. Naff
*Assistant Examiner*—Deborah K. Ware
(74) *Attorney, Agent, or Firm*—Fitch, Even, Tabin, & Flannery

(57) ABSTRACT

An aqueous extract of legumes is prepared for growing agronomically beneficial microorganisms. The extract is prepared by boiling a legume in water and removing solids. Preferably, 150 to 250 grams of legumes are boiled in about one liter of water for 15 to 30 minutes. The legumes include peas, beans, clover, alfalfa, and mixtures thereof. Also pea seeds can be prepared as a legume aqueous extract. A nitrogen source, a salt of an organic acid, an organic alcohol or mixtures thereof can be added to the extract-containing medium. Furthermore, the extract-containing medium is effective for growing agronomically beneficial microbes to a cell density of $10^8$ cells per milliter.

26 Claims, 1 Drawing Sheet

AQUEOUS EXTRACT OF LEGUMES FOR GROWING AGRONOMICALLY BENEFICIAL MICROBES

This application is a continuation-in-part application of U.S. Ser. No. 09/210,403, filed Dec. 11, 1998, now U.S. Pat. No. 5,951,978, which claims benefit of U.S. Provisional Application No. 60/111,776, filed Dec. 10, 1998.

The present invention relates mediums for the growth of microorganisms which are effective for improving plant productivity. More particularly, the invention provides a legume medium effective for the cultivation of agronomically beneficial microbes, such as Azospirillum.

BACKGROUND OF THE INVENTION

A number of microorganisms are known to have beneficial effects on plant growth. Among these are nitrogen fixing bacteria of the Rhizobium species, which are symbionts of leguminous species. Azospirillum species, which are free living nitrogen fixing bacteria associated with the roots of grasses, are also now recognized for their plant growth promoting qualities (Mishustin and Shilnikova, Moscow, Science Publ. House, 1973; Mishustin and Shilnikova, Moscow, Science Publ. House, 1968). More specifically, certain strains of *Azospirillum brasilense* have been shown to enhance accumulation of various minerals in wheat and soybean (Bashan et al., Applied and Environ. Microbiol., 56(3):769-775 (1990)), increase dry weights of maize shoots (O'Hara et al., Can. J. Microbiol., 27:871-877 (1981), and increase dry weights of sorghum, pearl millet and napier grass (Smith et al., Applied and Environ. Microbiol., 47(6): 1331-1336 (1984)).

Inoculation of seeds or soil with beneficial microorganisms, including Azospirillum, for crop improvement has been practiced for a number of years. However, variable and inconsistent results have often been observed possibly due to loss of inoculant viability or variability of dosage due to changes in inoculant viability (Okon et al., CRC Crit. Rev. Biotechnology, 6:61–85 (1987)).

Successful inoculation experiments appear to be those in which researchers have paid special attention to the optimal number of cells in the inoculant, using appropriate procedures to assure that cells remain viable for colonizing the roots (ASM News, Vol. 63, No. 7). Hence, the manner in which agronomically beneficial microorganisms are grown is critical to their viability and ultimate success in improving plant productivity.

Agronomically beneficial microbes have traditionally been cultured in synthetic mediums. For example, one of the most common mediums used for growing Azospirillum is NFb medium or a modification of NFb (Okon et al., Soil. Biol. Biochem., vol. 26, No. 12, pp. 1591–1601, 1994). These types of mediums do not provide microbes that consistently improve crop productivity. Further, synthetic mediums add to the cost of microbial inoculants.

SUMMARY OF THE INVENTION

The present invention is directed to a legume medium that is effective for optimal growth of microorganisms that are useful for increasing plant productivity and soil quality. Growth of agromonically benefical microbes on the legume medium of the present invention consistently and quickly provides high numbers of microbes in a physiological state that is optimal for increasing plant productivity. In an important aspect, the legume medium of the invention is effective for laboratory scale and large scale growth and propagation of microbes.

In accordance with the present invention, the legume medium is an aqueous extract of legumes that is prepared by boiling legume seeds, stems, leaves, and mixtures thereof in water. In this aspect of the invention, the legumes may include peas, beans, clover, alfalfa and mixtures thereof. In an important aspect of the invention, about 150 grams to about 250 grams of legumes are boiled in about one liter of water for about 15 to 30 minutes. After boiling, the medium is allowed to cool and solids are removed. The medium may be used directly for the propagation of agronomically beneficial microbes or optionally, may be further supplemented with a nitrogen source, a carbon source, or mixtures thereof.

In another important aspect, the present invention provides a method for growing agronomically beneficial microbes. In accordance with the method of the invention, an agronomically beneficial microbe is inoculated into a legume extract medium and cells are growth under conditions effective for providing a cell density of at least about $10^8$ cells/ml.

DETAILED DESCRIPTION

Definitions

Figure 1:
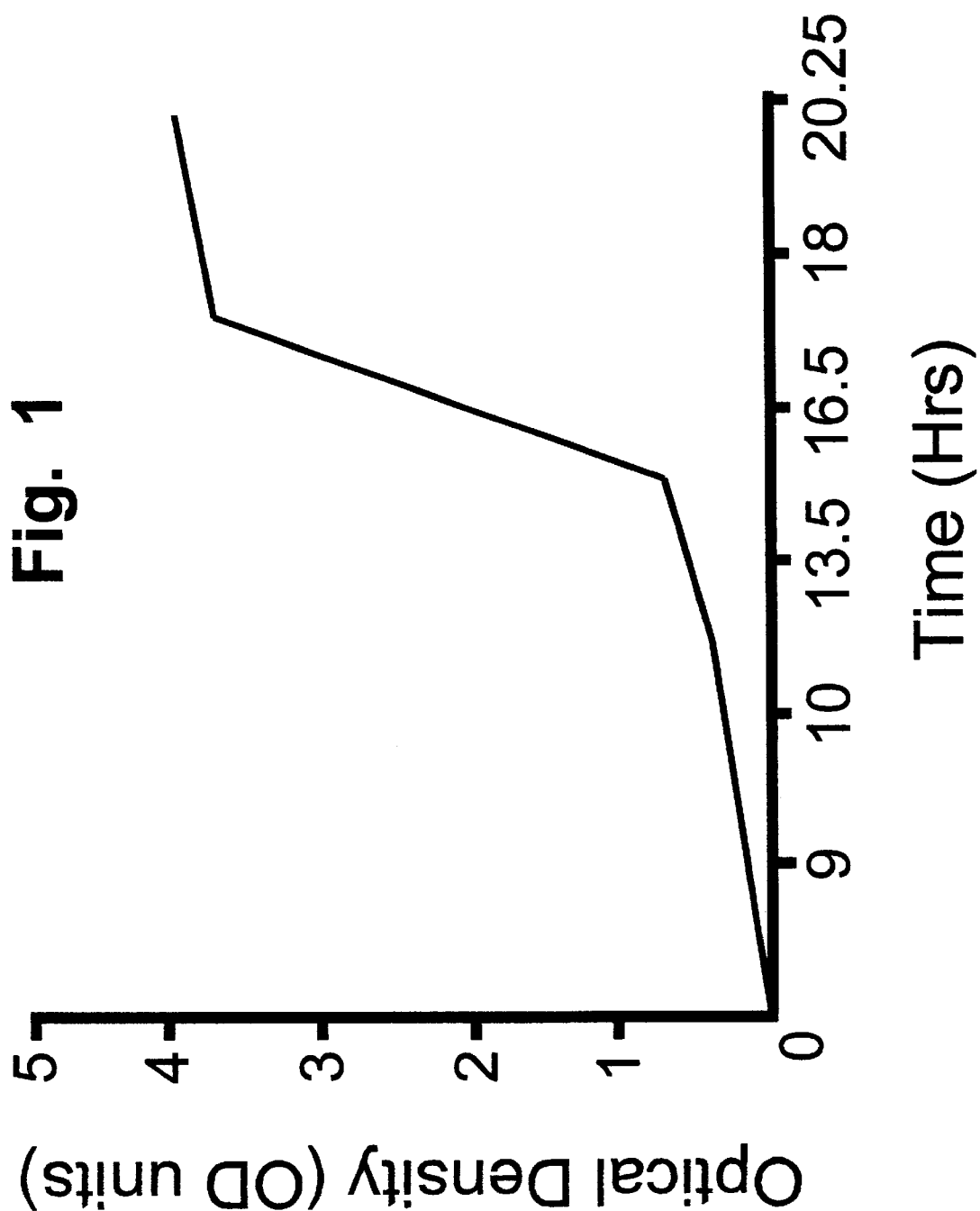
FIG. 1 is a growth curve of Azospirillum grown on the medium of the present invention.

As used herein an "agronomically beneficial strain" or "agronomically beneficial microbe" refers to microorganisms that are effective for increasing plant productivity. Microorganisms that provide agronomic benefit include symbiotic and nonsymbiotic microorganisms which may be effective for making nutrients more bioavailable to plants, and microorganisms that inhibit phytopathogenic microflora and stimulate plant growth. Examples of agronomically beneficial microorganisms include Azospirillum, Bacillus, Pseudomonas, Rhizobia, phototrophic and cellulose degrading bacteria, Clostridium, Trichoderma and the like, *Azospirillum brasilense*, and *Azospirillum brasilense* SAB MKB NRRL B-30082 and B-30081.

The term "plant productivity" or "crop productivity" refers generally to any aspect of growth or development of a plant that is a reason for which the plant is grown. For example, when referring to food crops, such as grains or vegetables, crop productivity generally refers to the yield of grain or fruit, etc., harvested from a particular crop. However, for "crops" such as turf grass, plant productivity may refer to growth rate, turf density, disease resistance and the like. Thus, for purposes of the present invention, improved plant or crop productivity refers broadly to improvements in yield of grain, fruit, flowers, or other plant parts harvested for various purposes, improvements in growth of plant parts, including stems, leaves and roots, improved resistance to disease, improved survivability in extreme climate, and similar improvements of the growth and development of plants.

"Improving soil quality" refers to increasing nitrogen levels in the soil and reducing the number of phytotoxic microorganisms.

As used herein "microbial inoculant" or "inoculum" refers to a preparation that includes agronomically beneficial microbes.

As used herein "biologically pure" refers to a microbial inoculant were a single strain of microbe is the only agronomically beneficial strain added to the inoculum.

Preparation of Medium

In an important aspect of the invention, the legume medium is prepared by boiling legumes. Legumes may include legume seeds, stems, leaves either individually or as a mixture. Legume roots are not effective for use in the medium. Types of legumes that may be used include peas, including sweet peas, chick peas, southern peas; beans, including soybeans and lima beans; clover; alfalfa; and mixtures thereof. In a very important aspect of the invention the legume used to prepare the medium is pea seeds.

In this aspect of the invention, about 150 to about 250 grams of legumes are boiled for about 15 to about 30 minutes in about one liter of water. In a very important aspect of the invention, about 200 grams of legumes are used per one liter of water and are boiled for about 20 minutes. After the medium cools to about room temperature, solids are removed. Solids may be removed by filtration or centrifugation by methods known in the art.

In an optional aspect of the invention, the legume medium may further a salt of an organic acid and added nitrogen. Appropriate salts of organic acids include calcium or sodium salts of malate, succinate, lactate, butyrate, propionate, ethanol, glycerol, citrate, isocitrate, fumarate and mixtures thereof. In an important aspect, the optimal sources of carbon for growth of agronomically beneficial microbes include sodium malate, sodium succinate, sodium lactate, glycerol and ethanol. In this aspect of the invention, the carbon source is about 0.25 weight percent to about 1 weight percent of the total weight of the medium, and in a very important aspect is about 0.5 weight percent of the medium.

Nitrogen sources that may optionally be added to the legume medium include ammonium salts, nitrate salts, peptone, yeast lysate, mixtures of nitrogen containing amino acids, and mixtures thereof. Specific nitrogen sources useful in the present invention include ammonium sulfate, ammonium chloride, potassium nitrate, uric acid, glycine, asparagine, glutamate, peptone, casein and mixtures thereof. In this aspect of the invention, the nitrogen source is about 0.05 weight percent to about 0.2 weight percent of the total weight of the medium, and in a very important aspect is about 0.1 weight percent of the medium. In another important aspect, the nitrogen source is ammonium sulfate.

Growth of Agronomically Beneficial Microbes

In an important aspect of the invention, agronomically beneficial microbes can be maintained and grown in a manner which is effective for maintaining the stability and consistency of the microbe. Even with repeated subculturing, microbes are stable in their ability to improve crop productivity through mechanisms such as fixing nitrogen, producing plant growth regulators, inhibiting phytotoxic organisms, and mixtures thereof.

In another important aspect of the invention, agronomically beneficial microbes can be easily grown on an industrial scale. This industrial scale method of culturing agronomically beneficial microbes is effective for providing a high rate of biomass per unit volume and provides a crop inoculum that is more tolerable to storage conditions.

In an important aspect of the invention, the inoculated legume extract medium is cultured at a time, temperature and aeration rate effective for providing a cell density having an optical density of at least about 3.0 or a cell density of at least about $10^8$ cells/ml. In an important aspect of the invention, culture time will typically range from about 10 to about 48 hours, temperatures are maintained at about ambient temperature, and standard aeration rates are used such that $O_2$ levels are not limiting. In another important aspect of the invention the legume medium is effective to provide a viable cell density of at least about $10^8$ cells/ml, but can typically provide viable cell densities of $10^9$ cells/ml to $10^{11}$ cells/ml. Doubling times of agronomically beneficial microbes can be as low as about 1 hour.

EXAMPLES

Example 1

Industrial Scale Growth of i Azospirillum brasilenseSAB MKB

Prep of Legume Extract Medium
1. Pea seeds were added to water (200 g/l) and boiled for 20 minutes.
2. Solid material were separated from the mixture (by filtration).

Culture Conditions
1. MKB was inoculated into 20 literes of the medium and grown with agitation and aeration at a temperature of 25° C. to 28° C. for 20.25 hours in a fermentors.
2. Cell densities reached an optical density of more than 4.0 to provide a cell density of $3.85 \times 10^9$ cells/ml. A graph of optical density versus time is provided in FIG. 1.

Example 2

Optimization Studies of Legume Medium

The following variations of legume medium were tested in shake flask culture to determine viable cell numbers of *Azospirillum brasilense* SAB MKB after approximately 24 hours.

| Medium | cells/ml |
| --- | --- |
| legume medium (no additions) | $3.85 \times 10^9$ |
| legume medium + 5 g/l glycerol + 1 g/l $(NH_4)_2SO_4$ | $2.03 \times 10^{10}$ |
| legume medium + 5 g/l Na succinate + 1 g/l $(NH_4)_2SO_4$ | $1.75 \times 10^{10}$ |

Numerous modifications and variations in practice of the invention are expected to occur to those skilled in the art upon consideration of the foregoing detailed description of the invention. Consequently, such modifications and variations are intended to be included within the scope of the following claims.

What is claimed is:

1. A microbial medium effective for growing agronomically beneficial microbes, the microbial medium comprising an aqueous extract of legumes, wherein the aqueous extract of legumes is prepared by boiling legumes in water and then removing solids, the microbial medium effective for providing agronomically beneficial microbes to a cell density of at least about $10^8$ cells/ml.

2. A microbial medium according to claim 1, wherein the legumes are selected from the group consisting of legume seeds, legume stems, legume leaves and mixtures thereof.

3. A microbial medium according to claim 2, wherein the legumes are selected from the group consisting of peas, beans, clover, alfalfa, and mixtures thereof.

4. A microbial medium according to claim 3, wherein about 150 grams to about 250 grams of legumes is boiled in about one liter of water for about 15 to about 30 minutes.

5. A microbial medium according to claim 4, wherein after boiling, the microbial medium is allowed to cool and solids are removed by filtration.

6. A microbial medium according to claim 1, wherein the legumes are pea seeds.

7. A microbial medium according to claim 1, wherein the microbial medium further comprises from about 0.05 weight percent to about 0.2 weight percent, based on the total weight of the microbial medium, of a nitrogen source.

8. A microbial medium according to claim 7, wherein the nitrogen source is selected from the group consisting of ammonium sulfate, ammonium chloridie, potassium nitrate, uric acid, glycine, asparagine, glutamate, peptone, casein and mixtures thereof.

9. A microbial medium according to claim 7, wherein the microbial medium further comprises about 0.1 weight percent, based on the total weight of the microbial medium, of an ammonium sulfate.

10. A microbial medium according to claim 1, wherein the microbial medium further comprises from about 0.25 weight percent to about 1 weight percent, based on the total weight of the microbial medium, of a salt of an organic acid, an organic alcohol, or mixtures thereof.

11. A microbial medium according to claim 10, wherein the salt of the organic acid is selected from the group consisting of calcium malate, calcium succinate, calcium lactate, calcium butyrate, calcium propionate, calcium citrate, calcium isocitrate, calcium fumarate, sodium malate, sodium succinate, sodium lactate, sodium butyrate, sodium propionate, sodium citrate, sodium isocitrate, sodium fumarate and mixtures thereof.

12. A microbial medium according to claim 10, wherein the microbial medium further comprises about 0.5 weight percent, based on the total weight of the microbial medium, of a sodium succinate.

13. A microbial medium according to claim 10, wherein the microbial medium further comprises about 0.5 weight percent, based on the total weight of the microbial medium, of a sodium succinate.

14. A microbial medium according to claim 10, wherein the organic alcohol is selected from the group consisting of ethanol, glycerol, and mixtures thereof.

15. A microbial medium prepared by a process comprising:
    boiling legumes in water from between about 15 to about 30 minutes; and removing solids, the microbial medium effective for providing agronomically beneficial microbes to a cell density of at least about $10^8$ cells/ml.

16. A microbial medium according to claim 15, wherein the legumes are selected from the group consisting of legume seeds, legume stems, legume leaves and mixtures thereof.

17. A microbial medium according to claim 15, wherein the legumes are selected from the group consisting of peas, beans, clover, alpalpha, and mixtures thereof.

18. A microbial medium according to claim 15, wherein about 150 grams to about 250 grams of legumes is boiled.

19. A microbial medium according to claim 15 wherein after boiling, the microbial medium is allowed to cool and the solids are removed by filtration.

20. A microbial medium according to claim 14, wherein the legumes are pea seeds.

21. A microbial medium according to claim 15, wherein the microbial medium further comprises from about 0.05 weight percent to about 0.2 weight percent, based on the total weight of the microbial medium, of a nitrogen source.

22. A microbial medium according to claim 21, wherein the nitrogen source is selected from the group consisting of ammonium sulfate, ammonium chloride, potassium nitrate, uric acid, glycine, asparagine, glutamate, peptone, casein and mixtures thereof.

23. A microbial medium according to claim 15, wherein the microbial medium further comprises about 0.1 weight percent, based on the total weight of the microbial medium, of an ammonium sulfate.

24. A microbial medium according to claim 15, wherein the microbial medium further comprises from about 0.25 weight percent to about 1 weight percent, based on the total weight of the microbial medium, of a salt of an organic acid, an organic alcohol, or mixtures thereof.

25. A microbial medium according to claim 24, wherein the salt of the organic acid is selected from the group consisting of calcium malate, calcium succinate, calcium lactate, calcium butyrate, calcium propionate, calcium citrate, calcium isocitrate, calcium fumarate, sodium malate, sodium succinate, sodium lactate, sodium butyrate, sodium propionate, sodium citrate, sodium isocitrate, sodium fumarate and mixtures thereof.

26. A microbial medium according to claim 24, wherein the organic alcohol is selected from the group consisting of ethanol, glycerol, and mixtures thereof.

\* \* \* \* \*